United States Patent [19]

Bonda et al.

[11] Patent Number: 5,788,954
[45] Date of Patent: Aug. 4, 1998

[54] HYDRATING SKIN CARE AND SUNSCREEN COMPOSITION CONTAINING DIBENZOYLMETHANE DERIVATIVE, E.G., PARSOL 1789, AND $C_{12}$, $C_{16}$, $C_{18}$ BRANCHED CHAIN HYDROXYBENZOATE AND/OR $C_{12}$, $C_{16}$, BRANCHED CHAIN BENZOATE STABILIZERS/SOLUBILIZERS

[75] Inventors: Craig A. Bonda, Wheaton; Steven P. Hopper, Glen Ellyn, both of Ill.

[73] Assignee: The C. P. Hall Company, Chicago, Ill.

[21] Appl. No.: 967,121

[22] Filed: Nov. 12, 1997

Related U.S. Application Data

[63] Continuation-in-part of Ser. No. 752,585, Nov. 21, 1996.
[51] Int. Cl.⁶ .............. A61K 7/42; A61K 31/24; A61K 31/12; A61K 7/00
[52] U.S. Cl. .............. 424/59; 424/60; 424/400; 424/401; 514/537; 514/679
[58] Field of Search .............. 424/59, 60, 400; 514/537, 679; 560/103; 568/331

[56] References Cited

U.S. PATENT DOCUMENTS

| | | | |
|---|---|---|---|
| 4,323,694 | 4/1982 | Scala, Jr. | 560/103 |
| 4,387,089 | 6/1983 | DePolo | 424/59 |
| 4,489,057 | 12/1984 | Welters et al. | 424/47 |
| 4,562,067 | 12/1985 | Hopp et al. | 424/59 |
| 5,116,604 | 5/1992 | Fugel et al. | 442/59 |

*Primary Examiner*—Shelley A. Dodson
*Attorney, Agent, or Firm*—Marshall, O'Toole, Gerstein, Murray & Borun

[57] ABSTRACT

A sunscreen composition containing a UV-A dibenzoylmethane derivative, such as 4-(1,1-dimethylethyl)-4'-methoxydibenzoylmethane (PARSOL® 1789), and a stabilizer/solubilizer for the dibenzoylmethane derivative having formula (I):

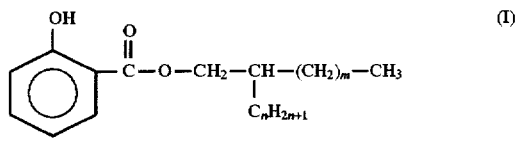

wherein
m=5, 7, 9 or mixtures and
n=4, 6, 8 or mixtures;

These long branched chain alkyl salicylates having a $C_4^+$ branch at the 2 position are quite effective in stabilizing the dibenzoylmethane derivative UV-B filter compounds making them more effective; effective for longer periods of time.

33 Claims, No Drawings

HYDRATING SKIN CARE AND SUNSCREEN COMPOSITION CONTAINING DIBENZOYLMETHANE DERIVATIVE, E.G., PARSOL 1789, AND $C_{12}$, $C_{16}$, $C_{18}$ BRANCHED CHAIN HYDROXYBENZOATE AND/OR $C_{12}$, $C_{16}$, BRANCHED CHAIN BENZOATE STABILIZERS/SOLUBILIZERS

CROSS REFERENCE TO RELATED APPLICATION

This application is a continuation-in-part of application Ser. No. 08/752,585 filed Nov. 21, 1996 now allowed.

FIELD OF THE INVENTION

The present invention is directed to a hydrating, stable sunscreen composition for topical application to human skin to protect the skin against UV radiation damage. The composition is particularly suitable for over-coating with make-up or other cosmetic compositions. More particularly, the present invention is directed to the use of a long chain ($C_{12}$, $C_{16}$ and/or $C_{18}$) branched alkyl salicylate that is surprisingly effective in stabilizing dibenzoylmethane derivatives, particularly 4-(1,1-dimethylethyl)-4'-methoxydibenzoylmethane (PARSOL® 1789) such that the PARSOL® 1789 is a more effective sunscreen, having a surprisingly increased sunscreen protection factor (SPF) and such that the PARSOL® 1789 is more effective over a longer period of time so that the sunscreen composition need not be applied to the skin as frequently. In a preferred embodiment, the composition also includes one or more branched chain alkyl benzoates for solvent/emollient properties that provides an exceptionally elegant skin feel.

BACKGROUND OF THE INVENTION AND PRIOR ART

It is well known that ultraviolet light having a wavelength between about 280 nm or 290 nm and 320 nm (UV-B) is harmful to human skin, causing burns that are detrimental to the development of a good sun tan. UV-A radiation, while producing tanning of the skin, also can cause damage, particularly to very lightly colored, sensitive skin, leading to reduction of skin elasticity and wrinkles.

Therefore, a sunscreen composition should include both UV-A and UV-B filters to prevent most of the sunlight within the full range of about 280 nm to about 400 nm from damaging human skin.

The UV-B filters that are most widely used commercially in sunscreen compositions are paramethoxycinnamic acid esters, such as 2-ethylhexyl paramethoxycinnamate, commonly referred to as octyl methoxycinnamate or PARSOL® MCX, having an ethyl radical extending from the 2 position of the hexyl long chain backbone; and octyl salicylate.

The UV-A filters most commonly used in commercial sunscreen compositions are the dibenzoylmethane derivatives, particularly 4-(1,1-dimethylethyl)-4'-methoxydibenzoylmethane (PARSOL® 1789), and 4-isopropyl dibenzoylmethane (EUSOLEX 8020). Other dibenzoylmethane derivatives described as UV-A filters are disclosed in U.S. Pat. Nos. 4,489,057; 4,387,089 and 4,562,067 and 5,670,140, hereby incorporated by reference. It is also well known that the above described and most commonly used UV-A filters, particularly the dibenzoylmethane derivatives, such as PARSOL® 1789, suffer in photochemical stability when combined with the above-described most commercially used UV-B filters. Accordingly, when a UV-B filter, such as 2-ethylhexyl paramethoxycinnamate (PARSOL® MCX), and/or octyl salicylate, is combined with the dibenzoylmethane derivative UV-A compounds, such as PARSOL® 1789, the PARSOL® 1789 becomes less photochemically stable necessitating repeated, frequent coatings over the skin for sufficient UV radiation protection.

In accordance with the principles of the present invention, it has been found, quite surprisingly, that by including a $C_{12}$, $C_{16}$, $C_{18}$ branched chain salicylate of formula (I), preferably $C_{12}$ branched chain salicylate, into a cosmetic sunscreen formulation containing a UV-A dibenzyolmethane derivative, particularly PARSOL® 1789, or EUSOLEX 8020, the dibenzyolmethane derivative is photochemically stabilized so that the dibenzyolmethane derivative-containing sunscreen composition is more effective for filtering out UV-A radiation; the composition filters UV-A radiation for longer periods of time; and, therefore, the sunscreen formulation need not be applied to the skin as frequently while maintaining effective skin protection against UV-A radiation:

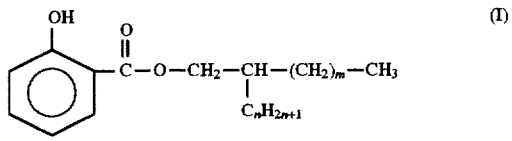

wherein m=5, 7, 9 or mixtures and n=4, 6, 8 or mixtures;

In the preferred embodiment, the sunscreen composition also contains about 1% to about 10% by weight of one or more alkyl benzoate solvent/emollient compounds having formula (II):

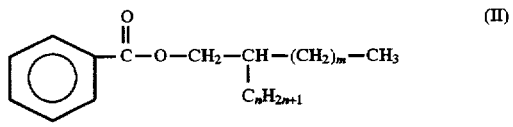

wherein m=5, 7 or mixtures and n=4, 6 or mixtures.

By the addition of the UV-B filter compounds, the cosmetic sunscreen formulation can maintain surprisingly effective skin protection against UV radiation both in the UV-A and UV-B range, with or without common sunscreen additives, such as benzophenone 3, octocrylene, and/or titanium dioxide. The ratio of UV-A to UV-B filter compounds is in the range of about 0.1:1 to about 3:1, preferably about 0.1:1 to about 0.3:1, most preferably about 0.24:1. Quite surprisingly, the compositions of the present invention maintain a high SPF, e.g., higher than 15, preferably at least 19, while containing relatively low concentration, e.g., 0.5–3% by weight of a UV-A absorber, such as PARSOL® 1789.

SUMMARY OF THE INVENTION

In brief, the present invention is directed to sunscreen compositions containing a dibenzoylmethane derivative UV-A filter compound, such as 4-(1,1-dimethylethyl)-4'-methoxydibenzoylmethane (PARSOL® 1789), and a salicylate stabilizer/solubilizer for the dibenzoylmethane derivative having formula (I):

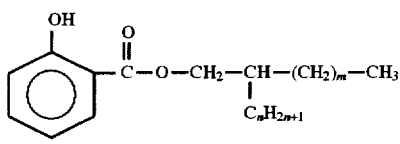

wherein m=5, 7, 9 or mixtures and n=4, 6, 8 or mixtures.

In accordance with a preferred embodiment of the present invention, the composition also includes about 1% to about 10% by weight of one or more branched chain alkyl benzoates for solvent/emollient properties having formula (II):

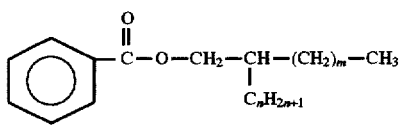

wherein m=5, 7 or mixtures and n=4, 6 or mixtures.

Surprisingly, it has been found that these long branched chain alkyl salicylates, such as butyloctyl salicilate, having at least $C_4$ branches at the 2 position, are quite effective in stabilizing the dibenzoylmethane derivative UV-A filter compounds making them more effective; effective for longer periods of time; and, therefore, the sunscreen composition need not be reapplied as frequently to maintain effective UV radiation skin protection.

Accordingly, one aspect of the present invention is to provide a stable, moisturizing sunscreen composition that includes a stabilizer/solubilizer salicylate compound having formula (I), capable of stabilizing a dimethylbenzoyl derivative UV-A filter, particularly PARSOL® 1789:

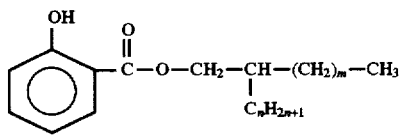

Another aspect of the present invention is to provide stabilizer compounds for dimethylbenzoyl derivatives, particularly PARSOL® 1789, and methods of manufacturing the stabilizer compounds, capable of stabilizing the dimethylbenzoyl derivatives, and capable of increasing the sunscreen protection factor (SPF) achievable for sunscreen compositions containing the dimethylbenzoyl derivatives to a SPF of at least 19, particularly 19–25 SPF.

Another aspect of the present invention is to provide a stable, moisturizing sunscreen composition that has a SPF of at least 19, without a sunscreen composition additive selected from the group consisting of benzophenone 3, octocrylene or other substituted dialkylbenzalmalonates or substituted dialkylmalonates.

Still another aspect of the present invention is to provide an improved, stable, moisturizing sunscreen composition containing 2-butyloctyl benzoate and/or 2-hexyldecyl benzoate, particularly a 40%, 60% by weight mixture, respectively, having a refractive index of at least about 1.40, particularly about 1.45 to about 1.48, that provides an exceptionally elegant skin feel to the moisturizer/sunscreen composition.

Another aspect of the present invention is to provide an improved, stable, moisturizing sunscreen composition containing butyloctyl salicylate, having a refractive index of about 1.49, that increases the effectiveness of dimethylbenzoyl derivative sunscreen compounds, particularly 4-(1,1-dimethylethyl)-4'-methoxydibenzoylmethane (PARSOL® 1789), in SPF and in duration.

Another aspect of the present invention is to provide an improved, stable sunscreen composition containing skin conditioning or skin care agents, including one or more biological polymers, such as sodium hyaluronate; and one or more biological additives (extracts) such as sunflower seed extract and/or wheat germ extract and/or myrrh extract and/or horsetail extract and/or phospholipids, e.g., Brookosome Herbal 1, without significant interference with the high SPF of the composition.

Still another aspect of the present invention is to provide a composition that conditions the skin in providing emollient, humectant and/or occlusive properties and maintains the skin soft, smooth and pliable while enhancing the appearance of dry skin with reduced flaking.

Another aspect of the present invention is to provide a homogenous composition that provides a high SPF, e.g. 19–25, emollient, and humectant skin care properties while including a very low concentration of surface active agents, less than about 1% by weight, preferably less than about 0.8% by weight, more preferably less than about 0.7% by weight, so that the composition is less irritating to sensitive skin.

Another aspect of the present invention is to provide a composition that has a high SPF, particularly useful for daywear/skincare, as well as beachwear/suncare that can be applied to the skin, particularly the face, to provide a cosmetically elegant appearance with a superb skin feel, which can be worn all day and is capable of receiving makeup thereover, and makeup can be applied more easily and more smoothly over the composition than directly over the face, thereby requiring less makeup for complete face coverage.

Another aspect of the present invention is to provide a skin care foundation composition that provides an SPF of at least 19, preferably at least 20, while including less than about 10% UV filter compounds, preferably less than about 9% UV filter compounds, more preferably less than about 8% UV filter compounds. Preferably the composition contains less than about 2% UV-A filter compounds, more preferably about 0.5% to about 1.5% UV-A filter compounds.

Another aspect of the present invention is to provide a moisturizing sunscreen composition containing an acrylate/$C_{10-30}$ alkyl acrylate crosspolymer (PEMULEN TR-1 from B.F. Goodrich) emulsifier that provides excellent emulsification of the moisturizing sunscreen composition while maintaining a high SPF. It has been found that the acrylate/$C_{10-30}$ alkyl acrylate crosspolymers emulsify the compositions of the present invention such that the composition can be spread over the skin without gas bubbles or voids so that complete coverage of the skin is achieved, without interfering with the high SPF provided by the sunscreen and stabilizer compounds of the composition.

Still another aspect of the present invention is to provide a moisturizing sunscreen composition that provides an SPF of at least 19 without octyl salicylate and contains less than 2% by weight avobenzone (PARSOL® 1789).

Another aspect of the present invention is to provide a moisturizing sunscreen composition that provides an SPF of at least 19 while incorporating less than about 8% by weight octyl methoxycinnamate.

The above and other aspects and advantages of the present invention will become more apparent from the following detailed description of the preferred embodiments.

DETAILED DESCRIPTION OF THE PREFERRED EMBODIMENTS

The sunscreen compositions of the present invention include about 0.5% to about 5%, preferably about 0.5% to about 3% of a dibenzoylmethane derivative UV-A filter compound, such as 4-(1,1-dimethylethyl)-4'-methoxydibenzoylmethane (PARSOL® 1789) and about 1% to about 10% by weight of a branched chain salicylate stabilizer/solubilizer for the dibenzoylmethane derivative, having formula (I):

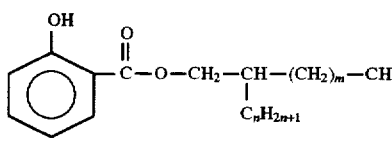
(I)

wherein m=5, 7, 9 or mixtures and n=4, 6, 8 or mixtures;

The compounds of formula (I) are formed by typical esterification and transesterification reactions as follows:

FORMULA (I)

1. Salicylate Esterification Reaction

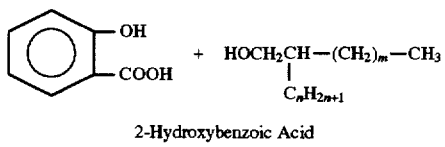

2-Hydroxybenzoic Acid where m=5, 7, 9 or mixtures and n=4, 6, 8 or mixtures

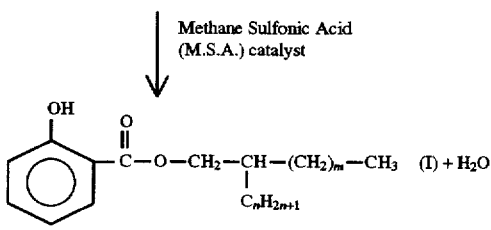

Methane Sulfonic Acid (M.S.A.) catalyst wherein m=5, 7, 9 or mixtures and n=4, 6, 8 or mixtures preferred where m=5 and n=4:

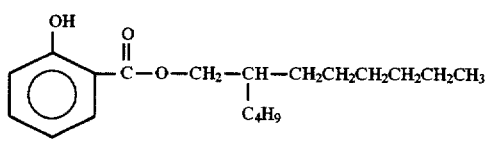

Butyloctyl Salicylate
(Refractive Index = 1.49)

Loading Formula For Butyloctyl Salicylate
(Preferred Formula (I)) Synthesis

| REACTANTS | WEIGHT % |
| --- | --- |
| Hydroxybenzoic Acid | 40.3 |
| 2-Butyloctanol (ISOFOL 12) | 59.7 |
| M.S.A.* (99.9%) | 0.2 |
| Sodium Hypophosphite | 0.015** |

*Methane sulfonic acid catalyst
**Based on the weight of hydroxybenzoic acid

Preferably, the compositions of the present invention include one or more branched chain alkyl benzoates of formula (II) that act as solvents and emollients in the composition:

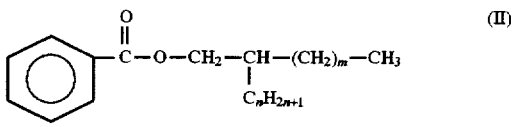
(II)

wherein m=5, 7 or mixtures and n=4, 6 or mixtures.

The benzoates of formula (II) can be synthesized as follows:

FORMULA (II)

1. Benzoate Esterification Reaction

Methyl Benzoate wherein m=5, 7 or mixtures and n=4, 6 or mixtures

Butyltin tris 2-ethylhexanoate catalyst

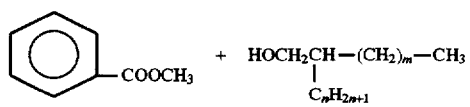

wherein m=5, 7 or mixtures and n=4, 6 or mixtures preferred mixtures are

40% by weight: m=5, n=4

60% by weight: m=7, n=6:

40% by weight 2-butyloctyl benzoate:

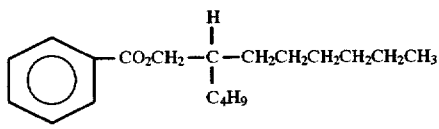

2-Butyloctyl Benzoate

60% by weight 2-hexyldecyl benzoate:

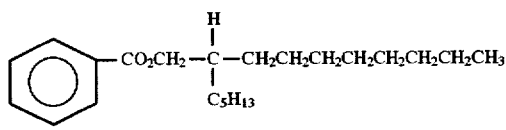

2-Hexyldecyl Benzoate

The 40%/60% mixture has a refractive Index of 1.48.

Loading Formula For 40% 2-Butyloctyl Benzoate/ 60% 2-Hexyldecyl Benzoate

| REACTANTS | WEIGHT % |
| --- | --- |
| Methylbenzoate | 40.8 |
| 2-Butyloctyl alcohol (ISOFOL 12) | 22.4 lbs. |
| 2-Hexyldecyl alcohol (ISOFOL 16) | 36.8 lbs. |
| Catalyst Fascat 9102* | 0.03%** |
| Sodium Hypophosphite | 0.015%** |
| SORBAMOL | 1.5%** |
| Dicalite | 0.75%** |

*Butyltin tris 2-ethylhexanoate catalyst
**Based on the weight of methyl benzoate + alcohols After loading the raw materials, agitation, nitrogen sparge and heat were turned on in a glass reaction kettle. Sodium hypophosphite was added on loading. At 290° F. the catalyst was added and heating was continued. Reaction started in the 380°–385° F. range as manifested by the evolution of MeOH. The overhead temperature was maintained at 140°–145° F. during the generation of MeOH. This was accomplished by controlling the reflux at 1:2 ratio. The reflux ratio indicates one fraction of the overhead product is taken out as a distillate product and two fractions goes back to the reaction kettle as reflux. This is the ratio found to be ideal to control the overhead temperature.

Heat was continued to a maximum reaction temperature of 420° F. When the overhead temperature dropped to 130°–135° F., the column was switched off and the reaction was continued on by-pass. Kettle samples were checked for acid value, color and percent alcohol. Vacuum was applied when the methyl alcohol content dropped to 2% by weight. Partial vacuum was applied initially to prevent foam over, then gradually increased to full as conditions permitted. Stripped for methylbenzoate until 0.10% by weight. At this time methylbenzoate odor was very faintly detectable. Cooled down the glass-lined reaction kettle to 180° F.

It is preferred to treat the product with a color body-absorbing compound, such as an activated charcoal or acid-activated calcium montmorillonite clay, to improve the color. The product required three separate activated charcoal treatments using 1% charcoal (based on batch initial weight) for each treatment to bring color down to 30–40 APHA. On the other hand, only one treatment with an acid-activated calcium montmorillonite clay (SORBAMOL) was required, in an amount of 1.2% based on the initial weight of the batch, to improve color to 20 APHA. All post treatment decolorizing steps were done at 180° F. and mixed for one hour, and then the batch was filtered with Dicalite.

The finished product was then analyzed and the results are as follows:

| Appearance | Clear |
| --- | --- |
| Acid Value | 0.01 |
| Color, APHA | 30–40 |
| Water, % | 0.03 |
| Saponification Value | 175.7 |
| Specific Gravity | 0.92 |
| Refractive Index | 1.48 |

One or more of the compounds of formula (I) are combined with moisturizers, emollients, solvents, lubricants, emulsifiers and/or other common cosmetic formulation ingredients for solubility of the formula (I) compound(s), one or more emulsifiers, thickening agents, and to provide other skin enhancement, e.g., moisturizing and humectant properties. The compositions can be produced as oily lotions, gels, solid sticks, emulsions, aerosols, and all other forms of cosmetic compositions. The compositions of the following examples provide exceptional skin feel, moisturizing and humectant properties in comparison to typical prior art sunscreen compositions.

EXAMPLE 1

| PHASE | CHEMICAL NAME | TRADE NAME | RANGE | PREFERRED RANGE | % WW | FUNCTION |
| --- | --- | --- | --- | --- | --- | --- |
| A. | Octyl methoxycinnamate | Escalol 557[1] | 1–10 | 1–8 | 6.00 | Sunscreen (UV-B) |
| A. | Butyloctyl salicylate | HALLBrite BHB[2]* | 1–15 | 1–10 | 7.50 | Solvent, emollient, |
| A. | Hexyldecyl benzoate & Butyloctyl benzoate | HALLStar AB[2]* | 0–10 | 1–10 | 5.00 | Solvent, emollient, |
| A. | Avobenzone | Parsol ® 1789[3] | 0.5–5 | 0.5–2 | 1.50 | Sunscreen (UV-A) |
| B. | PVP/Eicosene copolymer | Ganex V-220[1] | 0–2 | 0.01–2 | 0.40 | Moisture barrier |
| B. | Dimethicone copolyol | Silwet L-7087[4]* | 0–2 | 0.01–2 | 0.20 | Lubricant |
| B. | Tocopheryl acetate | Vitamin E acetate[5] | 0–2 | 0.01–2 | 0.20 | Vitamin |
| B. | Retinyl palmitate | Vitamin A palmitate[3] | 0–2 | 0.01–2 | 0.10 | Vitamin |
| B. | Bisabolol | alpha-Bisabolol[5] | 0–2 | 0.01–2 | 0.10 | Anti-inflammatory |

-continued

| PHASE | CHEMICAL NAME | TRADE NAME | RANGE | PREFERRED RANGE | % W/W | FUNCTION |
|---|---|---|---|---|---|---|
| B. | Sorbitan oleate | Span 80[6] | 0–5 | 0.1–5 | 0.40 | Particle size reducer |
| B. | Acrylates/C10–30 alkyl acrylates crosspolymer | Pemulen TR-1[7] | 0.1–5 | 0.1–1 | 0.25 | Emulsifier |
| B. | Silica | Aerosil R972[8] | 0–5 | 0.1–5 | 0.40 | Thickener |
| C. | Deionized water | Water | 50–80 | 60–70 | Q.S. | Solvent, carrier |
| C. | Xanthan gum | Rhodigel[9] | 0–2 | 0.01–2 | 0.10 | Stabilizer |
| C. | Cetyl hydroxyethylcellulose | Natrosol Plus[10] | 0–2 | 0.01–2 | 0.40 | Thickener, stabilizer |
| D. | Glycerin | Glycerin* | 0–10 | 1–10 | 4.00 | Humectant |
| D. | Butylene glycol | 1, 3 Butylene glycol* | 0–5 | 0.1–5 | 2.00 | Humectant, solvent |
| D. | Phenoxyethanol ( ) methyl-paraben ( ) ethylparaben ( ) propyl-paraben ( ) butylparaben | Phenonip[11] | 0–5 | 0.1–5 | 1.00 | Preservative |
| D. | Panthenol (50%) | D-Panthenol 50–P[5] | 0–5 | 0.1–5 | 0.50 | Moisturizer |
| E. | Triethanolamine (99%) | Triethanolamine* | 0–1 | 0.01–1 | 0.10 | Neutralizer |
| E. | Disodium EDTA | Disodium EDTA | 0–1 | 0.1–1 | 0.10 | Chelator |
| F. | Green tea extract | Phocyte Green tea[12] | 0–2 | 0.01–2 | 0.50 | Antioxidant |
| F. | Phospholipids & Horsetail extract & Myrrh extract & Sunflower seed extract & wheat germ extract | Brookosome Herbal 1[13] | 0–5 | 0.1–5 | 2.00 | Botanical Extracts |
| F. | Sodium hyaluronate (1%) | Na hyaluronate[14] | 0–1 | 0.001–1 | 0.50 | Moisturizer |
| F. | Acrylamide copolymer & Paraffin oil & Isoparaffin & Polysorbate 85 | Sepigel 501[15] | 0–2 | 0.01–2 | 0.50 | Thickener |

Preferred Mixing Sequence For All Examples

1. Stir "A" additives until Avobenzone is completely dissolved. Add "B" additives to "A", using propeller stirring to disperse Pemulen and silica completely. Heat to 55° C. with stirring.
2. With stirring, disperse and dissolve Xanthan gum in water. Heat to 80° C. Disperse Cetyl hydroxyethylcellulose in hot water Continue stirring with heat for 20 minutes. Remove from heat.
3. Blend "D" additives and add to "C" with stirring.
4. When Water Phase ("C" and "D") is at 55° C., add Oil Phase ("A" and "B") with vortex stirring. Continue stirring for 30 minutes.
5. Allow to cool while stirring. When temperature is below 40° C., add Triethanolamine. Stir to creamy smoothness. Stepwise, add Disodium EDTA to reduce viscosity.
6. Add "F" additives in order and blend in with stirring. Add fragrance.

1. ISP 2. C.P. HALL 3. Roche 4. OSi 5. BASF 6. ICI 7. B.F. Goodrich 8. DeGussa 9. Vanderbilt 10. Aqualon 11. Nipa 12. Collaborative 13. Brooks 14. Tri-K 15. Seppic *Available from C.P. HALL **SPF determined on human subjects by Harrison Research Laboratories, Union, N.J. Report available upon request. REF: CAB1-294 Daywear.frm In order to demonstrate that the branched chain salicylates of formula (I) photostabilize the dibenzoylmethane derivative UV-A filter compounds, such as PARSOL® 1789, two sunscreen formulations were prepared containing 2% avobenzone (dibenzoylmethane derivative—UV-A filter) incorporated in an oil phase consisting of 8% $C_{12-15}$ alkyl benzoate and an equal amount of another ester: octyl palmitate (Formulation A) or butyloctyl salicylate (Formulation B). Slides 7 mm square were prepared for each formulation by placing approximately 100 μl on a skin-like substrate (Vitro-skin, IMS) and spreading the material with a finger cot according to the established protocol. Measurements were made of each formulation using a Labsphere UV Transmittance Analyzer and the results were recorded. The slides were then placed in sunlight for two hours, following which measurements were again taken and the results were recorded.

The results were:

| Before Sun Exposure | Formulation A | Formulation B |
|---|---|---|
| Sun Protection Factor | 2.9 | 8.0 |
| UVA Absorbance | 88.26% | 88.63% |
| UVB Absorbance | 62.87% | 86.78% |

| After Sun Exposure | Formulation A | Formulation B |
|---|---|---|
| Sun Protection Factor | 0.9 | 4.8 |
| UVA Absorbance | 0.0% | 32.66% |
| UVB Absorbance | 23.25% | 83.75% |

As demonstrated by the data, Formulation B, containing butyloctyl salicylate, retains 60% of its Sun Protection Factor (SPF), 38% of is UV-A absorbance, and 97% of its UV-B absorbance following two hours of exposure to sunlight. In contrast, the formulation containing octyl palmitate retains only 31% of its SPF, none of its UV-A absorbance, and only 37% of its UV-B absorbance. The addition of butyloctyl salicylate to a formulation containing avobenzone clearly contributes to the photostability of the avobenzone and the maintenance of the efficacy of the formulation.

What is claimed is:

1. A sunscreen composition for topical application to human skin for protection against ultraviolet radiation and to provide skin moisturizing and elegant skin feel comprising, in a cosmetically acceptable carrier, at least about 0.5% by weight of a dibenzoylmethane derivative and at least about 0.5% by weight of a branched chain alkyl salicylate stabilizing compound of formula (I):

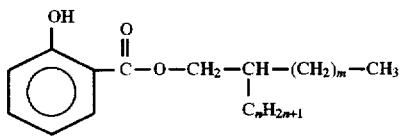

wherein
m=5, 7, 9 or mixtures and
n=4, 6, 8 or mixtures.

2. A composition in accordance with claim 1, wherein the molar ratio of said stabilizing compound having formula (I) to said dibenzoylmethane derivative is about 0.1:1 to about 3:1.

3. A composition in accordance with claim 1, wherein the molar ratio of said stabilizing compound having formula (I) to said dibenzoylmethane derivative is about 0.1:1 to about 0.3:1.

4. A composition in accordance with claim 3, wherein said dibenzoylmethane derivative is selected from the group consisting of 4-(1,1-dimethylethyl)-4'-methoxydibenzoylmethane; 4-isopropyl dibenzoylmethane; and mixtures thereof.

5. A composition in accordance with claim 4, wherein the dibenzoylmethane derivative is 4-(1,1-dimethylethyl)-4'-methoxydibenzoylmethane.

6. A composition in accordance with claim 5, wherein the dibenzoylmethane derivative is included in the composition in an amount of about 2% to 3% by weight of the composition.

7. A composition in accordance with claim 6, wherein the stabilizing compound is included in the composition in an amount of about 1% to about 10% by weight of the composition, and the stabilizing compound is butyloctyl salicylate.

8. A composition in accordance with claim 7, further including an emollient selected from the group consisting of 2-butyloctyl benzoate, 2-hexyldecyl benzoate, and mixtures thereof.

9. A composition in accordance with claim 8, including a mixture of 2-butyloctyl benzoate and 2-hexyldecyl benzoate in a weight ratio of 1:3 to 1:1.

10. A composition in accordance with claim 9, wherein the weight ratio is about 2:3.

11. A composition in accordance with claim 9, further including butyloctyl salicylate, in an amount of about 1% to about 10% by weight of the composition.

12. A method of filtering out ultraviolet radiation from human skin comprising topically applying to said skin a composition, in a cosmetically acceptable carrier, comprising 1% to 3% by weight of a dibenzoylmethane derivative and at least 1% by weight of a branched chain alkyl salicylate stabilizing compound of formula (I):

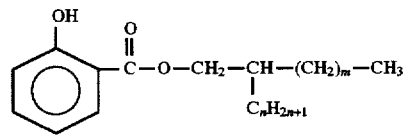

wherein
m=5, 7, 9 or mixtures and
n=4, 6, 8 or mixtures.

13. A method in accordance with claim 12, wherein the molar ratio of said stabilizing compound having formula (I) to said dibenzoylmethane derivative is about 0.1:1 to about 3:1.

14. A method in accordance with claim 12, wherein the molar ratio of said stabilizing compound having formula (I) to said dibenzoylmethane derivative is about 0.1:1 to about 0.3:1.

15. A method in accordance with claim 14, wherein said dibenzoylmethane derivative is selected from the group consisting of 4-(1,1-dimethylethyl)-4'-methoxydibenzoylmethane; 4-isopropyl dibenzoylmethane; and mixtures thereof.

16. A method in accordance with claim 15, wherein the dibenzoylmethane derivative is 4-(1,1-dimethylethyl)-4'-methoxydibenzoylmethane.

17. A method in accordance with claim 16, wherein the dibenzoylmethane derivative is included in the composition in an amount of about 0.5% to 3% by weight of the composition.

18. A method in accordance with claim 17, wherein the stabilizing compound is butyloctyl salicylate.

19. A method in accordance with claim 18, further including, in a total amount of about 1% to about 10% by weight of the composition, emollients comprising 2-butyloctyl benzoate and 2-hexyldecyl benzoate in a weight ratio of 2-butyloctyl benzoate to 2-hexyldecyl benzoate in the range of 1:3 to 1:1.

20. A method in accordance with claim 19, wherein the weight ratio is about 2:3.

21. A method in accordance with claim 19, further including butyloctyl salicylate, in an amount of about 1% to about 10% by weight of the composition.

22. A composition having emollient and sunscreen activity comprising a mixture of a compound of formula (I) and a compound of formula (II) in a weight ratio of (I):(II) in the range of 1:3 to 3:1

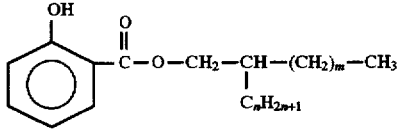

wherein
m=5, 7, 9 or mixtures and
n=4, 6, 8 or mixtures; and

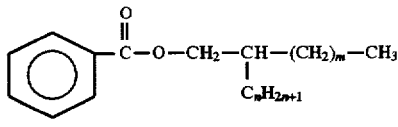

wherein
m=5, 7 or mixtures and
n=4, 6 or mixtures.

23. A composition in accordance with claim 22, wherein the compound of formula (II) includes a mixture of 2-butyloctyl benzoate and 2-hexyldecyl benzoate in a weight ratio of 1:3 to 1:1.

24. A composition in accordance with claim 23, wherein the weight ratio is about 2:3.

25. The composition of claim 23, further including a skin moisturizer, an emulsifying agent, a biological extract and a vitamin.

26. The composition of claim 25, wherein the skin moisturizer is selected from the group consisting of glycerine, butylene glycol, sodium hyaluronate, panthenol, and mixtures thereof, in an amount of about 0.1% to about 10% by weight of the composition.

27. The composition of claim 25, wherein the total concentration of the emulsifiers in the composition is less than about 1% by weight.

28. The composition of claim 27, wherein the total concentration of emulsifiers in the composition is less than about 0.8% by weight.

29. The composition of claim 28, wherein the total concentration of emulsifiers in the composition is less than about 0.7% by weight.

30. The composition of claim 25, wherein the biological extract is selected from the group consisting of green tea extract, phospholipids, horsetail extract, myrrh extract, sunflower extract, wheat germ extract, and mixtures thereof, in an amount of about 0.1% to about 10% by weight.

31. The composition of claim 25, wherein the vitamin is selected from the group consisting of retinyl palmitate, tocopheryl acetate, and mixtures thereof in an amount of about 0.1% to about 5% by weight.

32. A moisturizing sunscreen composition having the following composition:

| Chemical Name | % W/W |
| --- | --- |
| Octyl methoxycinnamate | 1–10 |
| Butyloctyl salicylate | 1–15 |
| Hexyldecyl benzoate & Butyloctyl benzoate | 0–10 |
| Avobenzone | 0.5–5 |
| Polyvinylpyrrolidone Eicosene copolymer | 0–2 |
| Dimethicone copolyol | 0–2 |
| Tocopheryl acetate | 0–2 |
| Retinyl palmitate | 0–2 |
| Bisabolol | 0–2 |
| Sorbitan oleate | 0–5 |
| Acrylate/$C_{10-30}$ alkyl acrylate crosspolymer | 0.1–5 |
| Silica | 0–5 |
| Water | 50–80 |
| Xanthan gum | 0–2 |
| Cetyl hydroxyethylcellulose | 0–2 |
| Glycerin | 0–10 |
| Butylene glycol | 0–5 |
| Phenylethanol()methyl-paraben()ethylparaben()propyl-paraben()butylparaben | 0–5 |
| Panthenol | 0–5 |
| Triethanolamine | 0–1 |
| Preservative | 0–1 |
| Green tea extract | 0–2 |
| A biological extract selected from the group consisting of: horsetail extract, myrrh extract, sunflower seed extract, wheat germ extract, and mixtures thereof | 0–5 |
| Sodium hyaluronate | 0–1 |
| Polyacrylamide | 0–2 |

33. The moisturizing sunscreen composition of claim 31 having the following composition:

| Chemical Name | % W/W |
| --- | --- |
| Octyl methoxycinnamate | 1-10 |
| Butyloctyl salicylate | 1-15 |
| Hexyldecyl benzoate & Butyloctyl benzoate | 1-10 |
| Avobenzone | 0.5-5 |
| Polyvinylpyrrolidone Eicosene copolymer | 0.01-2 |
| Dimethicone copolyol | 0.01-2 |
| Tocopheryl acetate | 0.01-5 |
| Retinyl palmitate | 0.01-5 |
| Bisabolol | 0.01-2 |
| Sorbitan oleate | 0.1-5 |
| Acrylate/$C_{10-30}$ alkyl acrylate crosspolymer | 0.1-5 |
| Silica | 0.1-5 |
| Water | 50-80 |
| Xanthan gum | 0.01-2 |
| Cetyl hydroxyethylcellulose | 0.1-5 |
| Glycerin | 1-10 |
| Butylene glycol | 0.1-5 |
| Phenoxyethanol()methyl-paraben()ethylparaben()propyl-paraben()butylparaben | 0.1-5 |
| Panthenol | 0.01-5 |
| Triethanolamine | 0.01-1 |
| Preservative | 0.01-1 |
| Green tea extract | 0.01-2 |
| A biological extract selected from the group consisting of: horsetail extract, myrrh extract, sunflower seed extract, wheat germ extract, and mixtures thereof | 0.1-5 |
| Sodium hyaluronate | 0.001-1 |
| Polyacrylamide | 0.01-2 |

* * * * *

UNITED STATES PATENT AND TRADEMARK OFFICE
CERTIFICATE OF CORRECTION

PATENT NO. : 5,788,954
DATED : August 4, 1998
INVENTOR(S) : Bonda, Craig A., et al.

It is certified that error appears in the above-identified patent and that said Letters Patent is hereby corrected as shown below:

Title page,
Item [56], References Cited, U.S. PATENT DOCUMENTS, insert
-- 5,670,140    9/1997    Deflandre et al.    424/59 --.

Signed and Sealed this

Twenty-seventh Day of April, 2004

JON W. DUDAS
*Acting Director of the United States Patent and Trademark Office*